United States Patent
Sato et al.

(10) Patent No.: US 10,002,446 B2
(45) Date of Patent: Jun. 19, 2018

(54) IMAGE PROCESSING APPARATUS AND METHOD OF OPERATION OF THE SAME

(71) Applicant: CANON KABUSHIKI KAISHA, Tokyo (JP)

(72) Inventors: Makoto Sato, Tokyo (JP); Yoshihiko Iwase, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 16 days.

(21) Appl. No.: 15/098,190

(22) Filed: Apr. 13, 2016

(65) Prior Publication Data

US 2016/0307341 A1 Oct. 20, 2016

(30) Foreign Application Priority Data

Apr. 15, 2015 (JP) ................. 2015-083720
Nov. 30, 2015 (JP) ................. 2015-234270

(51) Int. Cl.
| | |
|---|---|
| G06K 9/00 | (2006.01) |
| G06T 11/00 | (2006.01) |
| A61B 3/00 | (2006.01) |
| A61B 3/12 | (2006.01) |
| G06T 3/00 | (2006.01) |
| G06T 7/00 | (2017.01) |

(52) U.S. Cl.
CPC .......... *G06T 11/008* (2013.01); *A61B 3/0058* (2013.01); *A61B 3/1225* (2013.01); *G06K 9/00604* (2013.01); *G06T 3/0037* (2013.01); *G06T 3/0068* (2013.01); *G06T 7/0012* (2013.01); *G06T 2207/10101* (2013.01); *G06T 2207/20224* (2013.01); *G06T 2207/30041* (2013.01); *G06T 2207/30204* (2013.01)

(58) Field of Classification Search
CPC ................. G06K 9/00604; G06T 2207/20224
See application file for complete search history.

(56) References Cited

U.S. PATENT DOCUMENTS

| | | | | |
|---|---|---|---|---|
| 2005/0251010 | A1* | 11/2005 | Mistretta | ................ A61B 6/025 600/407 |
| 2007/0188707 | A1 | 8/2007 | Nanjo | |
| 2012/0253183 | A1 | 10/2012 | Muto | |
| 2013/0188141 | A1* | 7/2013 | Nakahara | ................. A61B 3/14 351/206 |

(Continued)

FOREIGN PATENT DOCUMENTS

| | | |
|---|---|---|
| EP | 2189110 A1 | 5/2010 |
| JP | 04-336677 A | 11/1992 |

(Continued)

*Primary Examiner* — Oneal R Mistry
(74) *Attorney, Agent, or Firm* — Canon U.S.A, Inc. IP Division (57) ABSTRACT

In an image processing apparatus, a display control unit controls displaying such that a subtraction image between a plurality of fundus images of an eye corresponding to a plurality of three-dimensional tomographic images obtained by capturing images of the eye at different times is displayed on a display unit, and a specifying unit specifies a plurality of two-dimensional tomographic images, in the plurality of three-dimensional tomographic images, to be displayed on the display unit, by a position specified on the displayed subtraction image.

34 Claims, 8 Drawing Sheets

(56) References Cited

U.S. PATENT DOCUMENTS

| | | | |
|---|---|---|---|
| 2013/0229622 A1* | 9/2013 | Murase | A61B 3/0033 |
| | | | 351/206 |
| 2013/0242259 A1* | 9/2013 | Hacker | A61B 3/102 |
| | | | 351/206 |
| 2015/0002813 A1 | 1/2015 | Ota | |
| 2015/0272434 A1* | 10/2015 | Satake | A61B 3/0058 |
| | | | 351/206 |
| 2015/0348293 A1* | 12/2015 | Sugahara | A61B 6/025 |
| | | | 345/424 |

FOREIGN PATENT DOCUMENTS

| | | |
|---|---|---|
| JP | 2002-230517 A | 8/2002 |
| JP | 2009-183332 A | 8/2009 |
| JP | 2010-220771 A | 10/2010 |

\* cited by examiner

IMAGE PROCESSING APPARATUS AND METHOD OF OPERATION OF THE SAME

BACKGROUND OF THE INVENTION

Field of the Invention

The present disclosure relates to an image processing apparatus configured to process an image of an eye, and a method of operating such an image processing apparatus.

Description of the Related Art

In a medical field, when some medical procedure is performed on a patient, a follow-up observation thereafter, that is, observing a reaction over time to the medical procedure is very important. In the field of diagnostic imaging, to make it easier to perform the follow-up observation, it is known to use a subtraction image, which is an image generated by determining a difference between a plurality of captured images obtained by capturing images of an object at different times. In a radiographic imaging field, Japanese Patent Laid-Open No. 2002-230517 discloses a subtraction image of chest X-ray images captured at different times.

In an ophthalmic field, Japanese Patent Laid-Open No. 04-336677 discloses a subtraction image of a fundus under examination between images captured at different times.

As for an imaging apparatus for use in the ophthalmic field, it is popular to use an optical coherence tomography (OCT) apparatus using interference of low coherence light. Regarding the follow-up observation using images captured using the OCT apparatus, Japanese Patent Laid-Open No. 2010-220771 discloses a method in which fundus images and tomographic images of a fundus captured at different times are displayed side by side on a monitor. Japanese Patent Laid-Open No. 2010-220771 also discloses a method in which difference information representing a difference in layer thickness distribution between tomographic images is displayed as layer thickness information in the form of a graph on a monitor.

SUMMARY OF THE INVENTION

In an aspect, the present disclosure provides an image processing apparatus including a generation unit configured to generate a subtraction image between a plurality of fundus images of an eye corresponding to a plurality of three-dimensional tomographic images obtained by capturing images of the eye at different times, a display control unit configured to control a display unit to display the subtraction image, and a specifying unit configured to specify a plurality of two-dimensional tomographic images, in the plurality of three-dimensional tomographic images, to be displayed on the display unit, by a position specified on the displayed subtraction image.

In an aspect, the present disclosure provides an image processing apparatus including a generation unit configured to generate a subtraction image between a plurality of fundus images of an eye corresponding to a plurality of three-dimensional tomographic images obtained by capturing images of the eye at different times, and a display control unit configured to control displaying such that a marker indicating a position of a two-dimensional tomographic image at least in one of the plurality of three-dimensional tomographic images is displayed on a display unit so as to be superimposed on the generated subtraction image.

In an aspect, the present disclosure provides a method of operating an image processing apparatus, including generating a subtraction image between a plurality of fundus images of an eye corresponding to a plurality of three-dimensional tomographic images obtained by capturing images of the eye at different times, controlling displaying so as to display the generated subtraction image on a display unit, and specifying a plurality of two-dimensional tomographic images, in the plurality of three-dimensional tomographic images, to be displayed on the display unit by a position specified on the displayed subtraction image.

In an aspect, the present disclosure provides a method of operating an image processing apparatus, including generating a subtraction image between a plurality of fundus images of an eye corresponding to a plurality of three-dimensional tomographic images obtained by capturing images of the eye at different times, controlling displaying so as to display the generated subtraction image on a display unit, and determining at least one two-dimensional tomographic image to be displayed on the display unit based on at least one of the plurality of three-dimensional tomographic images by being specified in terms of a position of a marker on the displayed subtraction image.

Further features of the present invention will become apparent from the following description of embodiments with reference to the attached drawings. Each of the embodiments of the present invention described below can be implemented solely or as a combination of a plurality of the embodiments or features thereof where necessary or where the combination of elements or features from individual embodiments in a single embodiment is beneficial.

DESCRIPTION OF THE EMBODIMENTS

In the ophthalmic field, with advances in OCT apparatuses, there is a need for a technique that allows a user to easily check both a plurality of tomographic images of an eye captured at different times, and a subtraction image between a plurality of fundus images of the eye corresponding to the plurality of tomographic images, thereby allowing the user to perform a high-efficiency follow-up observation.

In view of the above, an image processing apparatus according to an embodiment first generates a subtraction image between a plurality of fundus images of an eye corresponding to a plurality of three-dimensional tomographic images obtained by capturing images of the eye at different times. The image processing apparatus according to the embodiment displays the generated subtraction image on a display unit. The image processing apparatus according to the embodiment includes a specifying unit configured to specify or select a plurality of two-dimensional tomographic images from the plurality of three-dimensional tomographic images, to be displayed on the display unit, by specifying a position on the displayed subtraction image.

According to the present embodiment, a user is allowed to easily check both a plurality of tomographic images of an eye captured at different times, and a subtraction image between a plurality of fundus images of the eye corresponding to the plurality of tomographic images, thereby allowing the user to perform a high-efficiency follow-up observation.

The image processing apparatus and the operation method thereof according to the present embodiment are described in further detail below with reference to drawings. Note that in the embodiment described below, it is assumed by way of example that the image processing apparatus is connected to a tomographic imaging apparatus (an image generation unit 100) in such a manner that they are allowed to communicate with each other. However, the image processing apparatus and the tomographic imaging apparatus may be integrated into a single apparatus. For example, the image processing apparatus may be disposed in the tomographic imaging apparatus. Furthermore, in the present embodiment, it is assumed by way of example that the tomographic imaging apparatus is a polarization OCT apparatus which is one type of OCT apparatus. A description is given below for a case where a follow-up observation is performed using images representing polarization characteristics of an eye.

Overall Configuration

Figure 1:
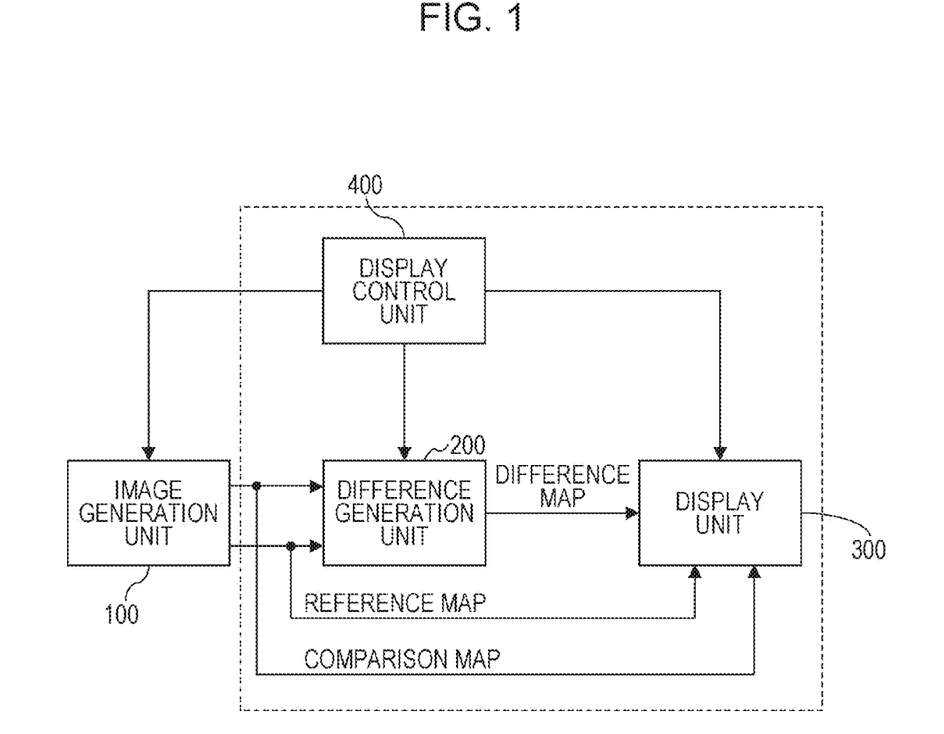
FIG. 1 is a diagram illustrating an overall configuration of an image processing apparatus according to an embodiment.

FIG. 1 is a diagram illustrating a configuration of an image capturing system including an image processing apparatus according to the present embodiment. In this figure, a part surrounded by a broken line is the image processing apparatus according to the present embodiment. In this figure, image data output from an image generation unit 100 is displayed on a display unit 300 for observation. The image data output from an image generation unit 100 is also input to a difference generation unit 200. The difference generation unit 200 generates a difference map and provides it to the display unit 300, which displays the difference map thereon.

A display control unit 400 controls a type of an image and a manner of displaying the image on the display unit 300 in accordance with an operation or the like performed by an operator. These functions may be realized using a personal computer (PC). In this case, the display unit 300 may be a display device such as a liquid crystal monitor or the like connected to the PC, and each part may be realized using software.

Next, a configuration and an operation of each unit are described in detail below.

Polarization OCT Apparatus

Figure 2:
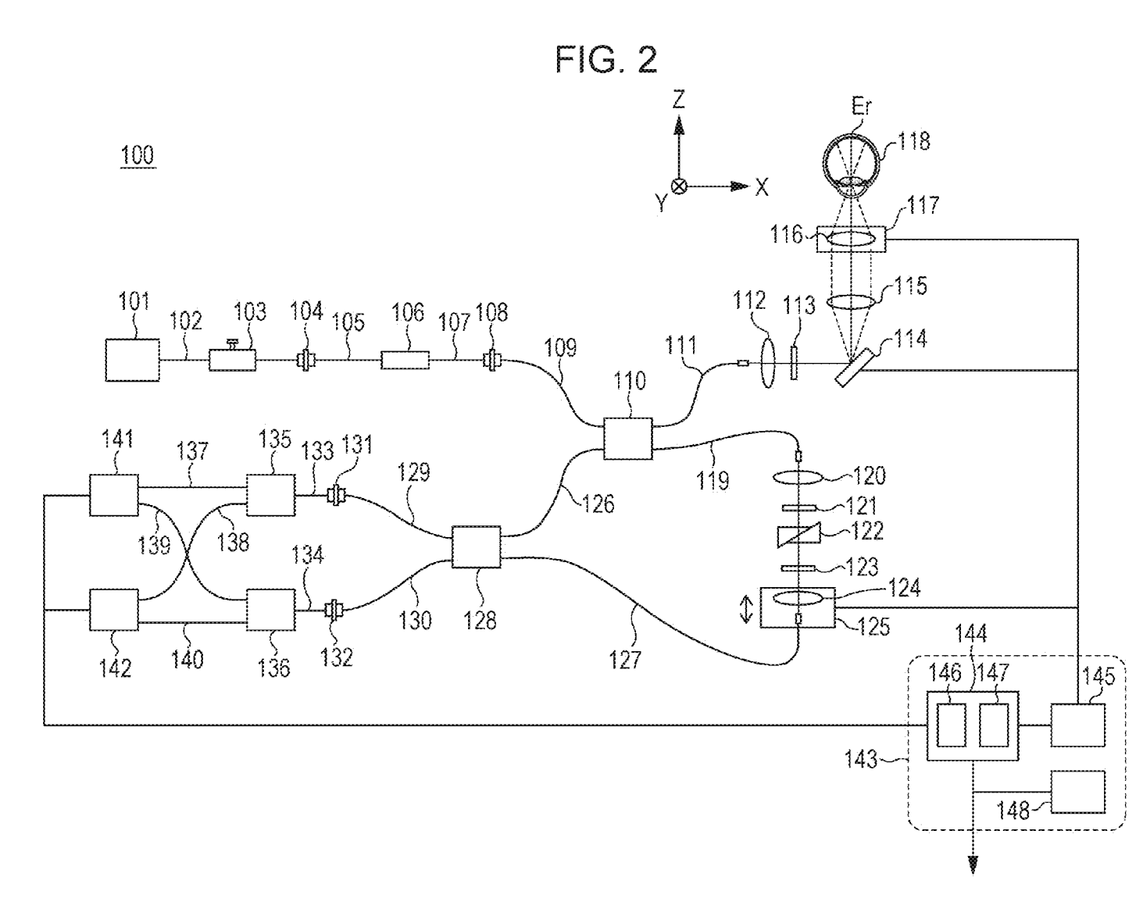
FIG. 2 is a diagram schematically illustrating a configuration of an OCT apparatus according to an embodiment.

FIG. 2 is a schematic diagram illustrating an overall configuration of a polarization OCT apparatus, which is an example of the image generation unit 100 according to the present embodiment. In the present embodiment, by way of example, a polarization OCT apparatus using SS (Swept Source)-OCT is described. Note that in the present embodiment, the polarization OCT apparatus is not limited to that based on SS-OCT, but SD (Spectral Domain)-OCT or TD (Time Domain)-OCT may be used. Note that although the polarization OCT apparatus is used as the image generation unit 100 in the present embodiment described below, the type of the OCT apparatus is not limited to the polarization OCT apparatus but a general type of OCT apparatus may be employed.

Overall Configuration of Apparatus

A light source 101 is a swept source (SS) light source that emits light while sweeping a wavelength over a range of 100 nm around a sweep center wavelength of 1050 nm. The light emitted from the light source 101 is transmitted to a beam splitter 110 via a single-mode fiber (SM fiber) 102, a polarization controller 103, a connector 104, an SM fiber 105, a polarizer 106, a polarization maintaining (PM) fiber 107, a connector 108, and a PM fiber 109, and is split into measurement light (also referred to as OCT measurement light) and reference light (also referred to as reference light corresponding to OCT measurement light). The beam splitter 110 splits the light at a splitting ratio of 90 (reference light): 10 (measurement light). A polarization controller 103 is capable of changing the polarization of the light emitted from the light source 101 to a particular polarization state. The polarizer 106 is an optical element having a characteristic that allows only a particular linearly polarized component to pass. A majority of the light emitted from the ordinary light source 101 is polarized in a particular polarization direction with a high degree of polarization. However, the light also includes a randomly polarized component that is not polarized in a particular polarization direction. It is known that the randomly polarized component causes degradation in image quality of a polarization OCT image. To handle this situation, the randomly polarized component is cut using the polarizer 106. Note that because only light in the particular linearly polarized state is allowed to pass through the polarizer 106, the polarization state is adjusted using the polarization controller 103 such that an optimum amount of light is incident on the eye 118 under examination.

The measurement light from the beam splitter is output via a PM fiber 111, and is collimated by a collimator 112. The collimated measurement light passes through a quarter-wave plate 113 and is incident on the eye 118 under examination via a galvano scanner 114 that scans the measurement light on a fundus Er of the eye 118 under examination, a scan lens 115, and a focus lens 116. Although it is described here that the galvano scanner 114 is a single mirror, the galvano scanner 114 actually includes two galvano scanners such that the fundus Er of the eye 118 under examination is raster-scanned. The focus lens 116 is disposed firmly on a stage 117 such that the focus lens 116 is allowed to move in a direction along the optical axis thereby making it possible to adjust the focus. The galvano scanner 114 and the stage 117 are controlled by a drive control unit 145 such that it is possible to scan the measurement light within a particular range (also referred to as a range in which a tomographic image is acquired, a position at which a tomographic image is acquired, or a position illuminated with measurement light) of the fundus Er of the eye 118 under examination. The quarter-wave plate 113 is an optical element having a characteristic that causes a phase delay of a ¼ wavelength to occur between an optical axis of the quarter-wave plate and an axis perpendicular to the optical axis. In the present embodiment, the optical axis of the quarter-wave plate is rotated about the optical axis by 45° with respect to the direction of the linear polarization of the measurement light emitted from the PM fiber 111 such that circularly-polarized light is incident on the eye 118 under examination. Although a detailed description is not given here, a tracking function may be provided to make it possible to detect a movement of the fundus Er and scan the mirror of the galvano scanner 114 so as to follow the movement of the fundus Er. The tracking may be performed using a common technique in real time or as post-processing. For example, it may be possible to employ a method using a scanning laser ophthalmoscope (SLO). In this method, for a fundus Er, a two-dimensional image in a plane perpendicular to an optical axis is acquired over time using the SLO, and a feature part such as a vessel bifurcation is extracted from the image. A moving distance of the fundus Er indicating how the feature part moves in the acquired two-dimensional image is calculated, and the calculated moving distance is fed back to the galvano scanner 114 thereby achieving the real-time tracking operation.

The measurement light is incident on the eye 118 under examination via the focus lens 116 disposed on the stage 117 and is focused on the fundus Er. The measurement light striking the fundus Er is reflected or scattered from each retinal layer, and returns to the beam splitter 110 via the optical path described above. The light returned to the beam splitter 110 is incident on a beam splitter 128 via a PM fiber 126.

The reference light from the beam splitter 110 is output via a PM fiber 119 and collimated by a collimator 120. The reference light is incident on a PM fiber 127 via a half-wave plate 121, a dispersion compensation glass 122, an ND filter 123, and a collimator 124. The collimator lens 124 and one end of the PM fiber 127 are fixed to an upper part of the coherence gate stage 125, and driven by the drive control unit 145 in a direction along the optical axis depending on a difference in the axial length of the eye of the subject. The half-wave plate 121 is an optical element having a characteristic that causes a phase delay of a ½ wavelength to occur between an optical axis of the half-wave plate and an axis perpendicular to the optical axis. In the present embodiment, the adjustment is performed such that the linearly polarized reference light output from the PM fiber 119 is brought into a polarization state in which the long axis is rotated by 45° in the PM fiber 127. Although the optical path length of the reference light is changed in the present embodiment, another configuration may be employed as long as the difference in the optical path length between the optical path of the measurement light and the optical path of the reference light is changed.

After passing through the PM fiber 127, the reference light is incident on the beam splitter 128. In the beam splitter 128, the returning measurement light and the reference light are combined, and, as a result, interfering light is generated. The generated interfering light is then split into two pieces of light such that the resultant two pieces of interfering light are opposite to each other in phase (hereinafter, respectively referred to as a positive component and a negative component). The positive component of the split interfering light is incident on a polarizing beam splitter 135 via a PM fiber 129, a connector 131, and a PM fiber 133. On the other hand, the negative polarized component of the interfering light is incident on a polarizing beam splitter 136 via a PM fiber 130, a connector 132, and a PM fiber 134.

In the polarizing beam splitters 135 and 136, the interfering light is split into two pieces of light according to the two polarization axes perpendicular to each other, that is, into a vertically polarized component (hereinafter referred to as a V-polarized component) and a horizontally polarized component (hereinafter referred to as H-polarized component). The positive interfering light incident on the polarizing beam splitter 135 is split by the polarizing beam splitter 135 into two pieces of interfering light, that is, a positive V-polarized component and a positive H-polarized component. The split positive V-polarized component is incident on a detector 141 via a PM fiber 137, while the positive H-polarized component is incident on a detector 142 via a PM fiber 138.

On the other hand, the negative interfering light incident on the polarizing beam splitter 136 is split by the polarizing beam splitter 136 into a negative V-polarized component and a negative H-polarized component. The negative V-polarized component is incident on the detector 141 via a PM fiber 139, while the negative H-polarized component is incident on the detector 142 via a PM fiber 140.

The detectors 141 and 142 are each a differential detection unit configured such that when two interference signals different in phase by 180° are input thereto, a common component is removed and only an interference component is output.

The V-polarized component of the interference signal detected by the detector 141 and the H-polarized component of the interference signal detected by the detector 142 are respectively output as electric signals corresponding to the strength of light, and input to a signal processing unit 144 which is an example of an image acquisition unit that acquires a three-dimensional tomographic image.

Control Unit 143

Next, a control unit 143 that controls the whole image generation unit is described below. The control unit 143 includes a signal processing unit 144, a drive control unit 145, and an image storage unit 148. The signal processing unit 144 further includes a fundus image generation unit 146 and a map generation unit 147. The fundus image generation unit 146 has a function of generating a luminance image and a polarization characteristic image from an electric signal transmitted from the signal processing unit 144, and the map generation unit 147 has a function of generating a map representing a polarization characteristics of a fundus retina. The image storage unit 148 has a function of storing generated various images in relation to information on the eye.

Generating Image

Next, an image generation process by the signal processing unit 144 is described. In the signal processing unit 144, the fundus image generation unit 146 performs a reconstruction process on the interference signals output from the detectors 141 and 142 thereby generating two tomographic images based on the respective polarized components, that is, a tomographic image corresponding to the H-polarized component and a tomographic image corresponding to the V-polarized component.

First, the fundus image generation unit 146 removes fixed pattern noise from the interference signals. The fixed pattern noise removal is performed as follows. The fixed pattern noise is extracted by averaging a plurality of detected A-scan signals, and the extracted fixed pattern noise is subtracted from the input interference signals. Note that the A-scan signal is data detected during one light source sweep period. Next, the fundus image generation unit 146 performs a window function process to optimize a depth resolution and a dynamic range, which are trade-off factors in a Fourier transform in a finite interval. Thereafter, FFT processing is performed to generate a tomographic signal.

The process described above is performed on the interference signals of the two polarized components. By scanning the galvano scanner 114, two two-dimensional tomographic images (hereinafter also referred to as B-scan) are generated. Based on the tomographic signals and the tomographic images, a luminance image and a polarization characteristic image are generated. The polarization characteristic image is an image representing a polarization characteristic of an eye. In the present embodiment, a tomographic image representing a degree of depolarization of an object (hereinafter such a tomographic image will be referred to as a DOPU image) is generated.

Figure 3A:
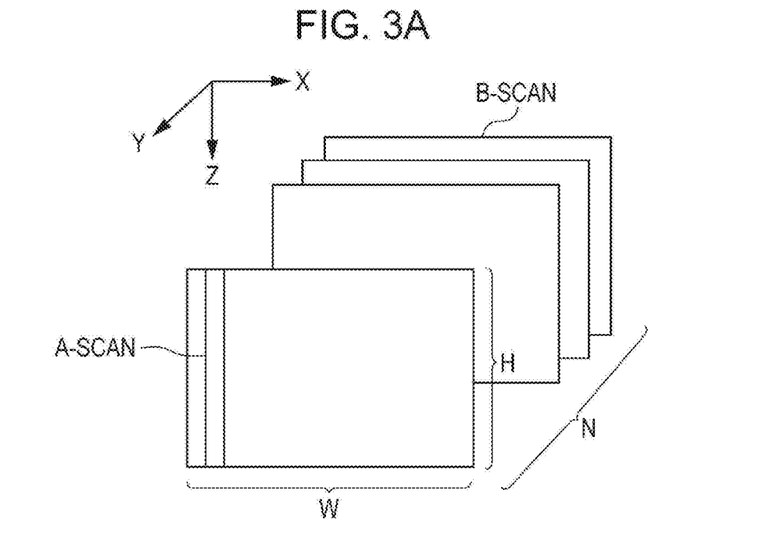
FIGS. 3A to 3D are diagrams illustrating generated images according to an embodiment.

FIG. 3A illustrates a relationship between A-scanning and B-scanning. Hereinafter, data including N pieces of B-scan data such as that shown in FIG. 3A will be referred to as volume data.

Generating Luminance Image

The fundus image generation unit 146 generates a luminance image from the two two-dimensional topographic signals described above. The luminance image is basically similar to a tomographic image based on conventional optical coherence tomography (OCT). Pixel values r thereof may be calculated from a tomographic signal $A_H$ of an H-polarized component and a tomographic signal $A_V$ of a V-polarized component respectively provided from the detectors 141 and 142 according to formula 1.

$$r = \sqrt{A_H^2 + A_V^2} \quad (1)$$

Volume data of a luminance image is generated by performing raster scanning using the galvano scanner 114 thereby obtaining a set of B-scan images, arranged in a sub-scanning direction, of the fundus Er of the eye 118 under examination.

Generating DOPU Image

The fundus image generation unit 146 generates a DOPU image from tomographic images of polarized components perpendicular to each other. A value d of each pixel of the DOPU image is obtained by digitizing the degree of depolarization of the object at a location corresponding to the pixel of the DOPU image. First, the fundus image generation unit 146 calculates a Stokes vector S at each pixel location of the tomographic image from tomographic signals $A_H$ and $A_V$ and a phase difference $\Delta\phi$ between them according to formula 2.

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix} \quad (2)$$

Next, the fundus image generation unit 146 sets a window with a length of about 70 μm in a main scanning direction of measurement light and a length of about 18 μm in a depth direction at the pixel location. Elements of the Stokes vector calculated according to formula (2) for each pixel are averaged, and the DOPU value d at the pixel location is calculated according to formula 3.

$$D = \sqrt{Q_m^2 + U_m^2 + V_m^2} \quad (3)$$

where $Q_m$, $U_m$, and $V_m$ are respectively average values of elements Q/I, U/I, and V/I of a Stokes vector in each window.

By performing the process described above for each pixel, a DOPU image corresponding to one B-scan is generated. The fundus image generation unit 146 performs the process described above for all B-scans as with the volume data of the luminance image thereby generating volume data of the DOPU image.

Generating Map

Figure 3B:
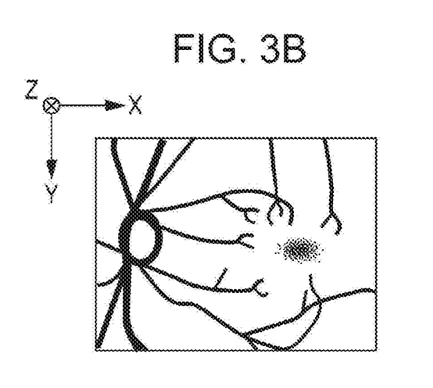
Figure 3C:
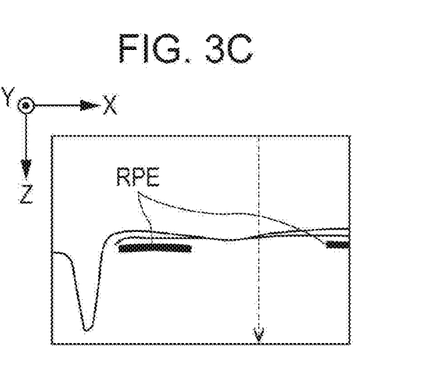
Figure 3D:
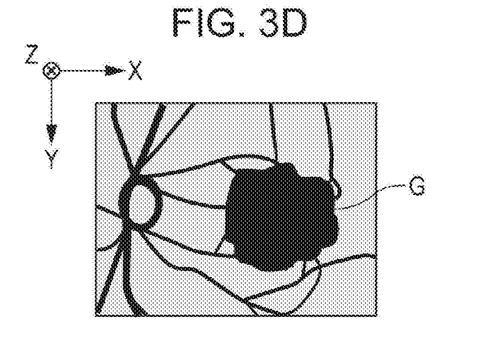

The map generation unit 147 generates a map of a fundus retina from the luminance image and the volume data of the DOPU image. The map is an image defined in an XY plane as illustrated in FIG. 3B or 3D, and pixel values thereof are determined by calculation from a set of volume data arranged in the Z axis. In the present embodiment, the map generation unit 147 generates a map from a luminance image and a DOPU image by a method described below. The map generation unit 147 generates a plan image by averaging, for each A-scan, the volume data of the luminance image (hereinafter such a plan image will be referred to as a pseudo SLO image). FIG. 3B illustrates an example of a pseudo SLO image, in which an image of a whole fundus is represented.

The map generation unit 147 also generates a map in terms of the thickness of a retinal pigment epithelium (RPE) from the volume data of the DOPU image. In this process, first, the map generation unit 147 performs a thresholding process on each B-scan data in the volume data of the DOPU image thereby generating a binary image in which pixels having DOPU values equal to or less than a specific threshold value (for example, 0.75) are extracted. This process is schematically illustrated in FIG. 3C. Because the RPE has a property of depolarization, the DOPU image has low pixel values. Such low pixel values are selectively extracted via the thresholding process as represented by black solid areas in FIG. 3C. Thereafter, the number of pixels extracted in the A-scan direction represented by a broken line in FIG. 3C is counted, and a RPE thickness map is generated by employing the count value as a pixel value of the map. FIG. 3D illustrates an example of a map generated in the above-described manner.

In this example, the RPE thickness map represents dry age-related macular degeneration having geographic atrophy (GA). In FIG. 3D, the map represents the GA area G as a region in which the RPE thickness is zero. In the above-described RPE extraction process, the threshold value is set to 0.75. However, the threshold value is not limited to this value. The threshold value may be experimentally determined in advance depending on an object. The map generation unit 147 may generate a drusen map in which a lesion part is extracted based on a DOPU image. A process of generating a drusen map is described below with reference to FIGS. 4A to 4D.

Figure 4A:
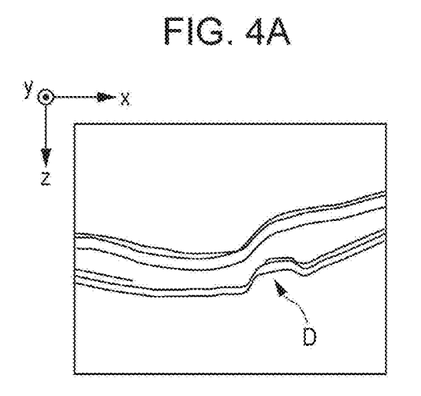
FIGS. 4A to 4D are diagrams illustrating a manner of generating a drusen map according to an embodiment.
Figure 4B:
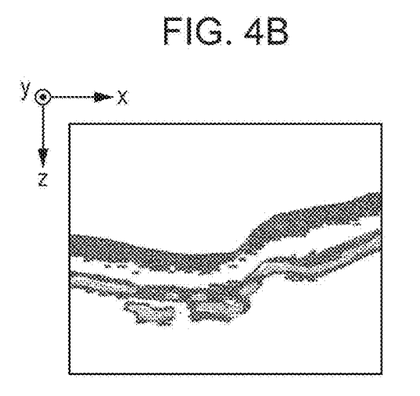
Figure 4C:
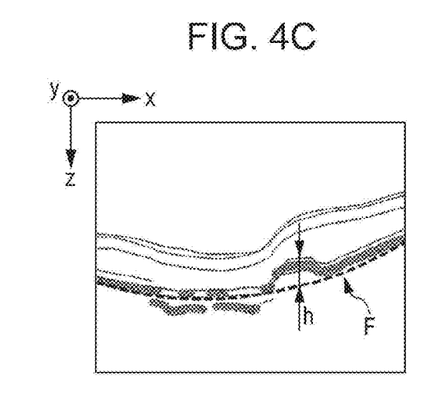
Figure 4D:
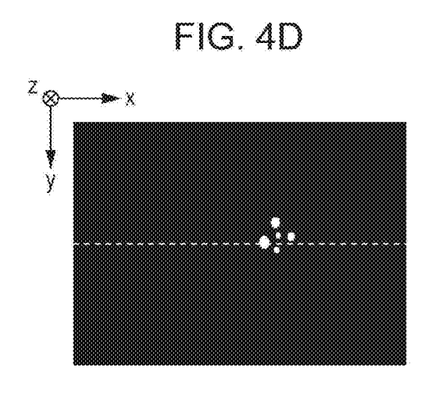

FIG. 4A illustrates an example of a B-scan image of a luminance image generated by the fundus image generation unit 146. In this example of the B-scan image, drusen D of a raised RPE is represented. FIG. 4B illustrates a B-scan image of a corresponding DOPU image. FIG. 4C illustrates a B-scan image in which a RPE is extracted via the thresholding process described above. As illustrated in FIG. 4C, the map generation unit 147 determines a line F that fits the extracted RPE by a polynomial approximation or the like, and further determines the distance h between the line F and the raised RPE extracted above. The map generation unit 147 then generates a drusen map by employing a value of the distance h as a pixel value of the drusen map. FIG. 4D illustrates an example of a drusen map generated in the above-described manner. In this example, a part where a drusen exists is represented as a white spot such that it is allowed to observe the position and the size of the drusen on the fundus. B-scanning represented by a broken line in FIG. 4D corresponds to FIGS. 4A to 4C.

Storing Image

The control unit 143 stores the interference signals output from the detectors 141 and 142, the volume data, and the maps generated in the above-described manner, in the image storage unit 148 in relation to eye identification information. The eye identification information includes, at least, information identifying a subject such as a name of the subject, a patient ID, or the like, a date/time when the data is acquired, and the like. The control unit 143 also has a function of, according to an instruction given by the display control unit 400, searching for captured image data of a specified eye taken at a particular date/time and outputting the retrieved captured image data.

Follow-Up Observation

Figure 5:
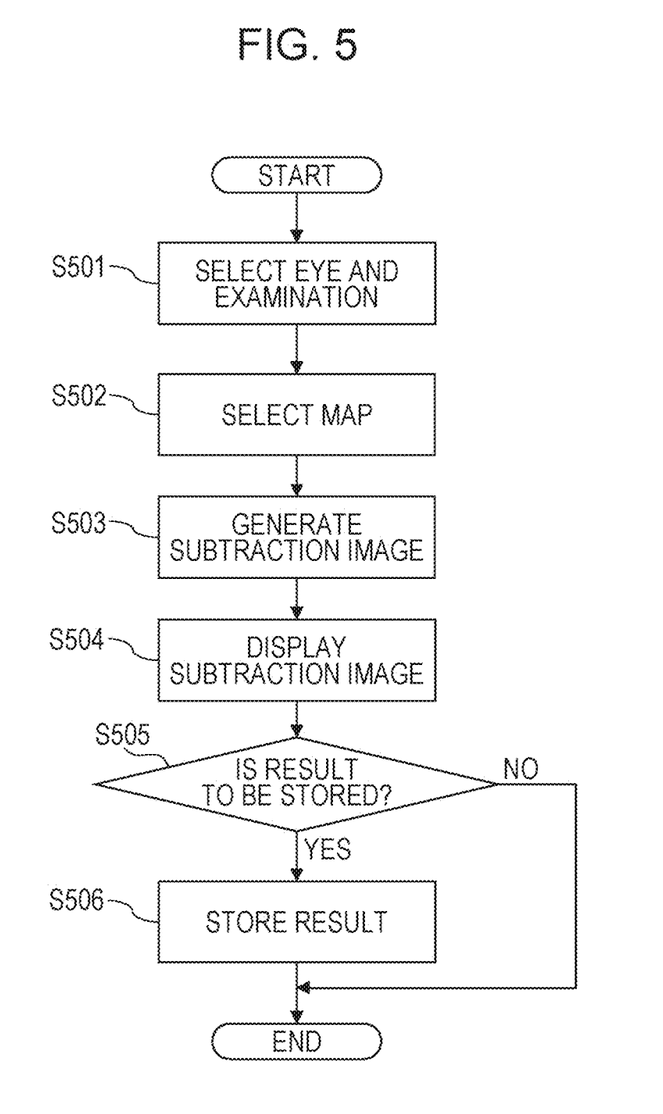
FIG. 5 is a flow chart illustrating a follow-up observation process according to an embodiment.
Figure 6:
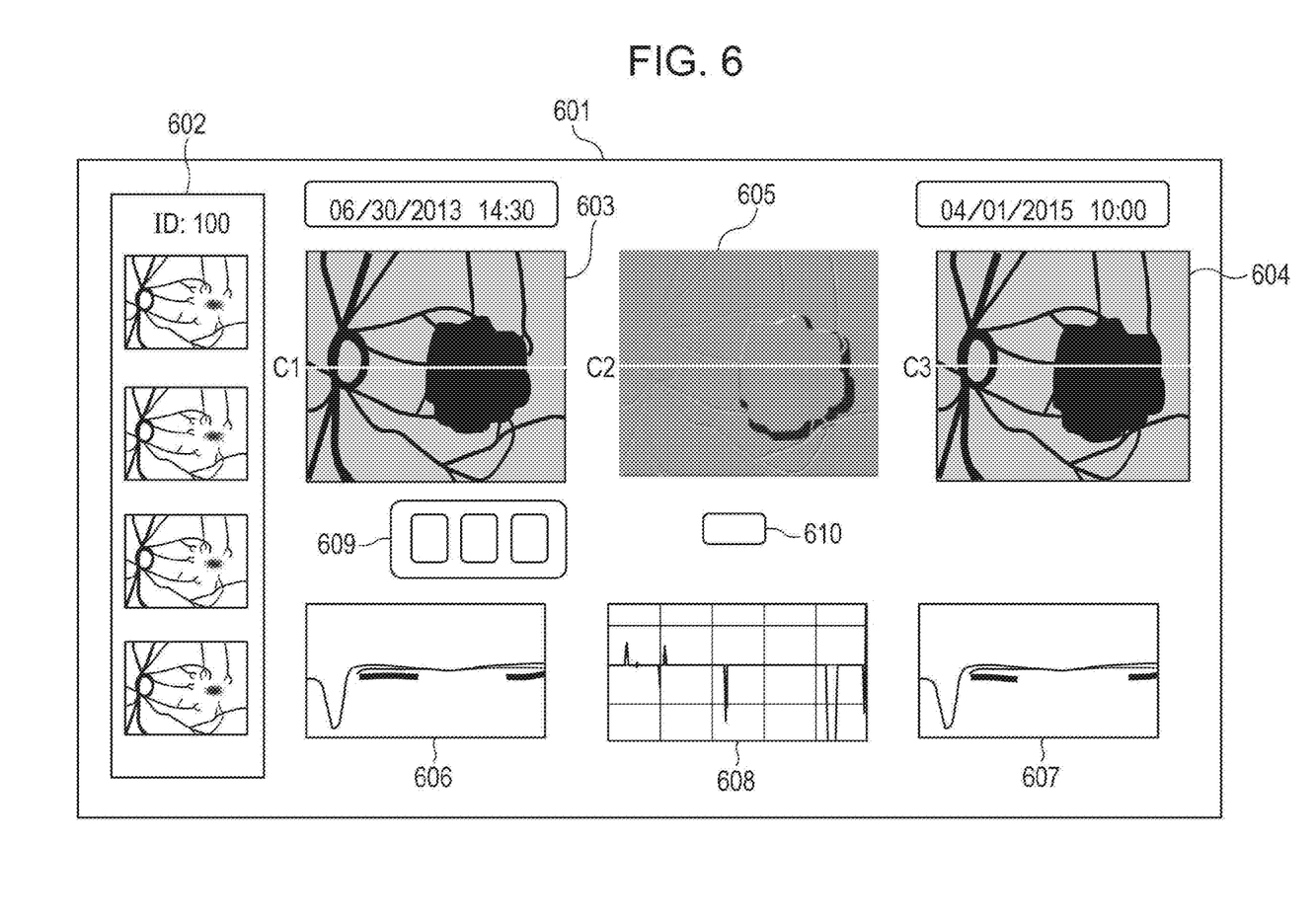
FIG. 6 is a diagram illustrating an example of a form in which an image processing apparatus displays images according to an embodiment.

Next, a follow-up observation process according to the present embodiment is described below with reference to FIG. 5 showing a flow chart, and FIG. 6 illustrating an example of a manner of displaying images on the display unit 300. This process is realized by an operation performed by the display control unit 400 in cooperation with the control unit 143, the difference generation unit 200, and the display unit 300. In a practical OCT apparatus, these functions may be realized using control software that runs on a single personal computer (PC) or using a control apparatus including one or more separate pieces of hardware. In the present embodiment, the functions are realized by control software that runs on a PC. A user is allowed to interactively execute various functions by using an input device such as a keyboard, a mouse or the like.

Screen Configuration

First, a screen configuration for use in follow-up observation according to the present embodiment is described. In FIG. 6, a follow-up observation screen 601 is a screen for use in follow-up observation, which is displayed on the display unit 300 by the display control unit 400. The follow-up observation screen 601 includes a selection area 602 for use in selecting an eye and a plurality of examinations performed at different times during a follow-up observation period, map display areas 603 and 604 in which maps associated with the selected examinations are displayed, and a difference display area 605 in which a difference (i.e. subtraction image) between selected maps is displayed. Hereinafter, the map display area 603 will be referred to as a reference map area and the map display area 604 will be referred to as a comparison map area to distinguish between them. Symbols C1 to C3 respectively represent cursors which are examples of markers displayed so as to be superimposed on a corresponding one of maps for use in specifying a position. The markers are displayed such that they are allowed to be moved on the respective maps. Data corresponding to the position specified by the cursor is displayed in a data display area located below a corresponding map. By moving the cursor, which is an example of a marker, on the subtraction image displayed on the display unit 300 using an input device such as a mouse or the like, which is an example of a specifying unit, it is possible to specify a two-dimensional tomographic image to be displayed on the display unit 300 (i.e. reference display area 606, comparison display area 607, difference data display area 608). Herein it may be desirable to further provide a detection unit (not shown) for detecting a position specified on the subtraction image by the marker. The two-dimensional tomographic image corresponding to the detected position may be determined by selecting at least one two-dimensional tomographic image from a plurality of two-dimensional tomographic images forming a three-dimensional tomographic image. Alternatively, the two-dimensional tomographic image corresponding to the detected position may be determined by reconstructing a two-dimensional tomographic image using a three-dimensional tomographic image. The cursor displayed so as to be superimposed on the subtraction image displayed in the difference display area is an example of a first marker. Cursors displayed so as to be superimposed on fundus images respectively displayed in the reference map display area 603 and the comparison map area 604 are each an example of a second marker. It may be desirable that when the first marker on the displayed subtraction image and at least one of second markers on the displayed fundus images are moved, the other one of the second markers is moved synchronously.

The data display areas are, for example, a reference data display area 606, a comparison data display area 607, and a difference data display area 608. A set of radio buttons 609 (a set of map selection buttons) allows the selection of one of map types to be displayed in map display areas. In the present embodiment, it is allowed to select one of three types: luminance image; RPE thickness map; and drusen map. A difference calculation execution button 610 is for executing a difference calculation.

Next, a flow of follow-up observation according to the present embodiment is described below. Note that in FIG. 6, the difference display area 605 is disposed between the reference map area 603 and the comparison map area 604, although the present disclosure is not limited to this arrangement. In the follow-up observation, it is necessary to first detect a part where a change occurs. Therefore, it may be desirable to dispose the difference display area near a center of a screen on which a user tends to focus with his/her eyes. The display control unit 400 may display the plurality of specified two-dimensional tomographic images and the plurality of fundus images side by side for each examination (for each time when the images are captured) on the display unit. For example, the display control unit 400 may display the reference map area 603 and the reference data display area 606 side by side for the same examination on the display unit, and may display the comparison map area 604 and the comparison data display area 607 side by side on the display unit for the same examination.

The layout of the reference map area 603, the comparison map area 604, and the difference display area 605 may be changed in accordance with a user's preference. For example, the reference map area 603 and the comparison map area 604 may be disposed side by side, and the difference display area 605 may be disposed in an edge area of the screen. In this case, for example, the difference display area 605 may be disposed next to the comparison map area 604 on a side opposite to the side where the reference map area 603 is located. In a case where a user wants to make a comparison between the reference map and the comparison map more preferentially than other comparisons, the above-described layout allows the user to make the comparison with a less amount of eye movement than in the case where the subtraction image is disposed between the reference map area 603 and the comparison map area 604. For a user who wants to preferentially check a subtraction image, it may be desirable to display the subtraction image between the reference map area 603 and the comparison map area 604 as described above. The change of the layout setting in the above-described situation may be performed by the display control unit 400 according to an input given by a user via a not-shown user interface. A setting file in which parameters in terms of the layout of display areas are described may be provided, and a user or an administrator may modify the content of the file to change the layout.

Step S501: Selecting Eye and Examination

When the display control unit 400 receives inputs, given by a user, specifying an eye and an examination, the display control unit 400 selects captured image data according to the inputs. In the present embodiment, information such as an ID or the like identifying a subject is input in the selection area 602 as illustrated in FIG. 6, and, in response, thumbnail images of various examinations are displayed such that it is allowed to specify an examination by selecting a thumbnail image. Each thumbnail image is accompanied with a superimposed examination date/time (not shown). A user is allowed to make an examination selection by dragging and dropping an examination used as a reference in comparison into the reference map area 603 and an examination to be subjected to the comparison into the comparison map area 604 using the input device such as a mouse or the like. The thumbnail images may be stored in the image storage unit 148 by the image generation control unit 413 when corresponding images are captured. When a particular subject is selected, the display control unit 400 may read out volume data, that is, three-dimensional tomographic image data from the image storage unit 148, and may generate and display thumbnail images.

Via the operation described above, the display control unit 400 reads out the selected maps from the image storage unit 148 and displays them in the corresponding map display areas. The display control unit 400 also reads out the volume data from which the maps are generated, and displays the volume data in the reference data display area 606 and the comparison data display area 607. When the maps are displayed in the respective map display areas such that the types specified via the set of map selection buttons 609 are displayed, B-scan images of positions corresponding to the position specifying cursors C1 and C3 superimposed on the maps are displayed in the reference data display area 606 and the comparison data display area 607.

Step S502: Selecting Map

A user is allowed to change the type of a map displayed in each map display area by operating a button in the set of map selection buttons 609. In the present embodiment, as described above, it is allowed to select a type from the group including the luminance image, the RPE thickness map, and the drusen map. FIG. 6 shows a state in which the RPE thickness map is selected by way of example. To change the type of the map, instead of using buttons, any other method such as a drop-down list, a list box, or the like may be used as long as it is allowed to select one item from a plurality of items.

Step S503: Generating Subtraction Image

Figure 7A:
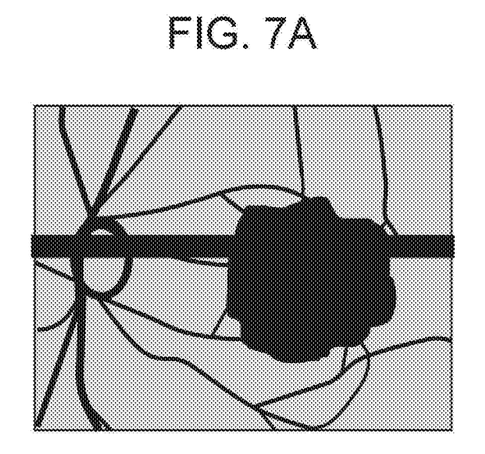
FIGS. 7A and 7B are diagrams illustrating blinking in an image in a process of determining a difference according to an embodiment.

When a user presses down a difference calculation execution button 610, the display control unit 400 instructs the difference generation unit 200 to start the process of determining the difference between selected maps. The difference generation unit 200 adjusts a relative position between the two selected maps, and generates a difference map (subtraction image) by subtracting pixel values of the reference map from pixel values of the comparison map at respective corresponding positions, and employing resultant pixel values as pixels value of the difference map. In the relative position adjustment described above, a pseudo SLO image may be used regardless of the selected map type. In this case, there is a possibility that a subject person under examination may blink during a process of capturing volume data. If blinking occurs, the map may include a stripe of invalid data such as that illustrated in FIG. 7A. It may be desirable not use such invalid data in the relative position adjustment, because an eyelid of the subject person prevents light from returning correctly from the blinking eye and the resultant image includes substantially no signal during the blinking. The stripe area extends in parallel to the main scanning direction of the galvano scanner, and the difference generation unit 200 detects such an invalid area and uses the other area in the relative position adjustment. The difference generation unit 200 stores information indicating the location of the detected invalid area. The display control unit 400 stores, in an internal memory (not shown), information indicating the relative positional relationship between the reference map and the comparison map identified in the relative position adjustment, and the display control unit 400 relates the position specifying cursors C1 to C3 to the relative positional relationship.

Step S504: Displaying Subtraction Image

The produced difference map (subtraction image) is displayed in the difference display area 605. In this state, values of the difference map at the position indicated by the position specifying cursor C2 are displayed in the form of a graph (two-dimensional tomographic image) in the difference data display area 608. In FIG. 6, by way of example, a result of calculating a difference between RPE thickness maps is shown. In this example, a GA area represented in the comparison map is greater than that in the reference map. Therefore, difference values are negative for parts whose area increases, while difference values are nearly equal to zero for parts where no change or only a small change occurs. In the present embodiment, the display control unit 400 represents the difference map in 256-level gray scale such that a difference value of 0 corresponds to a middle of the gray scale, a predetermined maximum value corresponds to a maximum gray level, that is, 255, and a minimum value corresponds to a gray level of 0. In this setting, a part where an expansion in a GA occurs is represented in black, while other parts are represented in halftone. Thus, a user is allowed to intuitively recognize the part where the change has occurred.

When a user adjusts the position by operating one of the cursors C1 to C3, the display control unit 400 synchronously moves the other cursors based on the stored positional relationship such that the other cursor point to the same position on the eye as that indicated by the one of the cursors. Therefore, a user is allowed to easily recognize a part where a large change occurs on the reference map or the comparison map by operating the cursor on the difference map. To allow a user to observe a different area of each map, an additional button (not shown) for turning on or off the synchronous movement operation described above may be provided in the follow-up screen 601. The button is an example of a switching unit for enabling or disabling the synchronous movement.

Note that in steps S501 and S502, a positional relationship between selected maps is not known, and thus it may be desirable that it is allowed to independently move the cursors without being synchronized. In this case, by changing the manner of displaying the cursors (for example, the color, the thickness, the type, or the like thereof) before and after the positional relations is determined in step S504, it becomes possible for a user to understand whether data displayed in the data area is corresponding data or not. A slider may be provided on each data display area (606 to 608) such that a user is allowed to operate the slider to select a tomographic image or a graph. In this case, it may be desirable that the sliders are synchronized with the position specifying cursors C1 to C3.

Figure 7B:
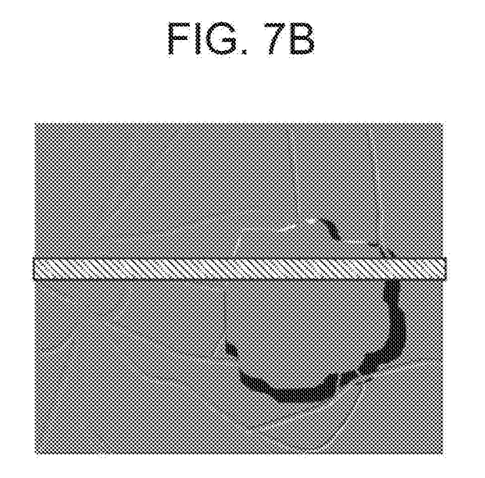

In a case where an invalid area is stored by the difference generation unit 200, the display control unit 400 displays this area on the difference map of this area in such a manner that it is allowed to distinguish the area from the other parts. For example, the invalid area may be displayed in the form of a stripe shaded with diagonal lines as illustrated in FIG. 7B such that a user is allowed to easily distinguish this part from the other parts. The invalid area may be displayed in a different manner as long as a user is allowed to recognize the invalid area. For example, an error message or the like may be displayed as a display form to indicate that there is an invalid area in the difference display area 605. In the example shown in FIG. 6, the selection area 602 is disposed in a leftmost area of the screen and thumbnail images are arranged vertically in this selection area 602. Alternatively, the selection area 602 may be disposed in an upper area of the screen and thumbnail images may be arranged horizontally in the selection area 602.

Step S505: Determining Whether to Store Result

A user selects whether or not a result of a process of determining a difference is stored in the image storage unit 148. In a case where the result is to be stored, the processing flow proceeds to step S506, but otherwise the processing flow of the follow-up observation is ended. The selection may be performed by the user by operating a storage button (not shown) or the like.

Step S506: Storing Result

The display control unit 400 stores the generated difference map together with information identifying the maps used in the generation in the image storage unit 148. In this process, information indicating the positional relationship between the two maps may also be stored. This makes it possible to synchronously move the position specifying cursors when the difference map is displayed again without performing the subtraction process.

As described above, according to the present embodiment, a user is allowed to effectively observe a change between a plurality of maps. Although the RPE thickness map has been described above by way of example, similar effects are also achieved when the embodiment is applied to a drusen map or a pseudo SLO. The types of the map are not limited to those described above. For example, the embodiment is also applicable to a map obtained by segmenting volume data of a luminance image into retinal layers and generating a map only for a particular layer (for example, retinal nerve fiber layer), a map obtained by extracting unrelated parts from a plurality of pieces of volume data and a vascular map representing a vascular area is generated, etc.

Figure 8:
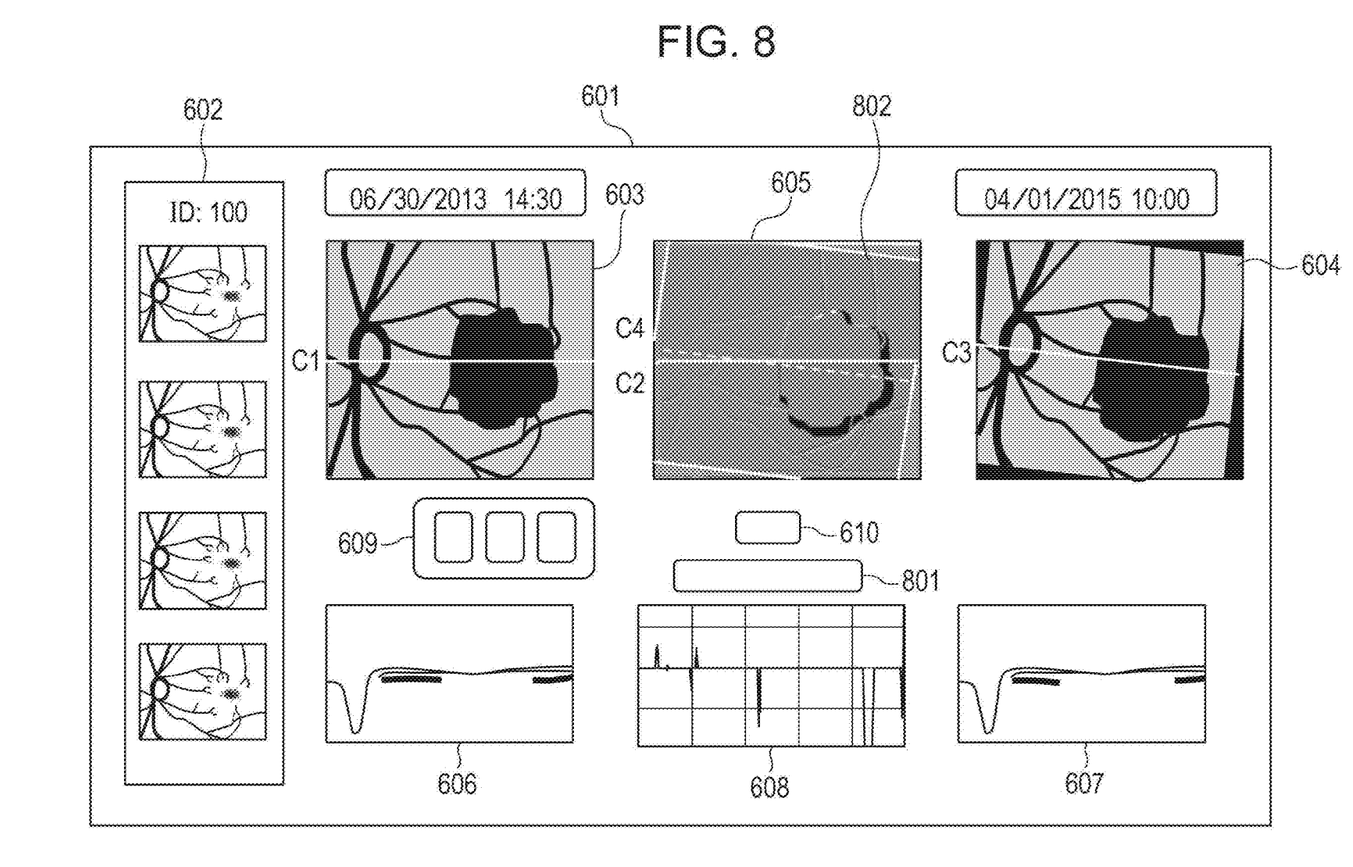
FIG. 8 is a diagram illustrating an example of a form in which an image processing apparatus displays images according to an embodiment.

Furthermore, it may be allowed to visually recognize a shift between two examinations in terms of a relative position between the reference map and the comparison map. It may be allowed to specify a type of data displayed in each data display area (606 to 608). FIG. 8 illustrates another example of a manner of displaying data in the image processing apparatus according to the present embodiment. The display control unit 400 displays the comparison map in the comparison map area 604 such that after the relative position adjustment between the comparison map and the reference map is performed in step S503 as described above, the resultant comparison map represented in corrected coordinates is displayed in the comparison map area 604. In the example shown in FIG. 8, the comparison map has a clockwise rotation with respect to the reference map, which means that the comparison map was generated based on an image of an eye taken in a situation in which the eye had a relative rotation. In this situation, the difference generation unit 200 functions as an example of a position shift information acquisition unit and calculates corresponding points of the reference map and the comparison map using a known process based on an affine transformation, and the difference generation unit 200 obtains position shift information including at least the shift information and the rotation information of the comparison map relative to the reference map. The comparison map is generated by performing at least shifting and rotating with reference to the reference map based on the acquired information associated with the position shift information.

In the comparison data display area 604 and the difference display area 605, cursors C3 and C4 may be displayed recognizably to indicate a position of B-scan as of the time when the comparison data is acquired, thereby making it possible for a user to more precisely recognize the positional relationship between the difference map and the comparison data.

Furthermore, the display control unit 400 may display, in a superimposed fashion, a contour line 802 (which is an example of a display form that indicates a range of the comparison map) to indicate a position (an outer frame) of the comparison map in the difference display area 605. This makes it possible for a user to recognize the positional relationship of the comparison map with respect to the reference map. In this configuration, an area outside the contour line 802 of the comparison map is a part in which the reference map and the comparison map do not have a common area, and thus the display control unit 400 may display this part in a predetermined color. In FIG. 8, this part is shaded, by way of example, in gray although other colors (such as black) may be employed.

Furthermore, in FIG. 8, a tomographic image switching unit 801 for selecting the type of an image displayed in the data display area may be provided to make it possible for a user to select an image from a set of selectable images given, for example, in the form of a pull-down list or the like. The selectable images may include a result of extracting an RPE such as that shown in FIG. 3C, a result of extracting a drusen such as that shown in FIG. 4C, a luminance image such as that shown in FIG. 4A, and the like.

In response to the selection via the tomographic image switching unit 801, the types of images displayed in the map display areas 603 and 604 may be changed accordingly. For example, when an RPE extraction result is selected by the tomographic image switching unit 801, RPE thickness maps may be displayed in the reference map area 603 and the comparison map area 604. On the other hand, in a case where a tomographic image of luminance information is selected via the tomographic image switching unit 801, luminance image maps (pseudo SLO images) may be displayed in the reference map area 603 and the comparison map area 604. The result of the selection performed via the tomographic image switching unit 801 may be automatically applied to the set of map selection buttons 609. By making it possible for a user to select the type of an image displayed, it becomes possible for the user to observe details of a depth-direction state of a part where a change occurs between examinations.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to embodiments, it is to be understood that the invention is not limited to the disclosed embodiments. The scope of the following claims is to be accorded the broadest interpretation s as to encompass all such modifications and equivalent structures and functions.

This application claims the benefit of Japanese Patent Application No. 2015-083720, filed Apr. 15, 2015 and Japanese Patent Application No. 2015-234270, filed Nov. 30, 2015 which are hereby incorporated by reference herein in their entirety.

What is claimed is:

1. An image processing apparatus comprising:
a generation unit configured to generate a subtraction image between a plurality of fundus images of an eye corresponding to a plurality of three-dimensional tomographic images obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light;
a display control unit configured to control a display unit to display the subtraction image and to display a marker indicating a position of at least one of a plurality of two-dimensional tomographic images in a state of being superimposed on the subtraction image; and
a specifying unit configured to specify, by a position of the marker being specified on the displayed subtraction image, at least one of the plurality of two-dimensional tomographic images in at least one of the plurality of three-dimensional tomographic images,
wherein the display control unit is configured to control the display unit to display the specified at least one of the plurality of two-dimensional tomographic images.

2. The image processing apparatus according to claim 1, wherein
the specifying unit is configured to specify, by the marker being moved on the displayed subtracted image, at least one of the plurality of two-dimensional tomographic images in at least one of the plurality of the three-dimensional tomographic images.

3. The image processing apparatus according to claim 1, wherein the display control unit is configured to control displaying such that the subtraction image and a display form representing the difference between the specified plurality of two-dimensional tomographic images are displayed side by side on the display unit.

4. The image processing apparatus according to claim 3, wherein the display control unit is configured to control displaying such that the display form representing the difference is displayed between the displayed plurality of two-dimensional tomographic images.

5. The image processing apparatus according to claim 3, wherein the marker indicates a position of the display form representing the difference in the subtraction image.

6. The image processing apparatus according to claim 3, wherein the display control unit is configured to control displaying such that a graph representing the difference between the specified plurality of two-dimensional tomographic images is displayed as the display form representing the difference on the display unit.

7. The image processing apparatus according to claim 2, wherein
the display control unit is configured to control displaying such that the specified plurality of two-dimensional tomographic images and the plurality of fundus images are displayed side by side on the display unit for each capture time, and
a first marker and a second marker are displayed on the display unit such that the first marker is superimposed on the subtraction image and the second marker is superimposed on the plurality of fundus image so as to indicate positions of the plurality of two-dimensional tomographic images.

8. The image processing apparatus according to claim 7, wherein the display control unit is configured to control displaying such that when the first marker on the subtraction image moves, the second marker is moved on the plurality of fundus images synchronously with the movement of the first marker and such that when the second marker on the plurality of fundus images moves, the first marker is moved on the subtraction image synchronously with the movement of the second marker.

9. The image processing apparatus according to claim 7, further comprising
a switching unit configured to switch between a mode in which the synchronous movement is enabled and a mode in which the synchronous movement is disabled,
wherein the display control unit changes a display form representing the first marker and the second marker depending on whether the synchronous movement is enabled or disabled.

10. The image processing apparatus according to claim 7, wherein
the plurality of fundus images are two fundus images, and
the display control unit is configured to control displaying such that the subtraction image is displayed between the two fundus images.

11. The image processing apparatus according to claim 7, further comprising
a selection unit configured to select a type of images to be displayed as the plurality of fundus images,
wherein the display control unit is configured to control displaying such that, according to the selected types, a plurality of maps generated using the plurality of three-dimensional tomographic images are displayed as the plurality of fundus images.

12. The image processing apparatus according to claim 7, further comprising
a position shift information acquisition unit configured to acquire position shift information including at least rotation information indicating a rotation of a first one of the plurality of fundus images with respect to a second one of the plurality of fundus images,
wherein the display control unit is configured to control displaying such that the first one of the plurality of fundus images is displayed on the display unit so as to be at least rotated based on the position shift information, and a display form representing a range of the second one of the plurality of fundus images is displayed on the display unit so as to be superimposed on the generated subtraction image.

13. The image processing apparatus according to claim 1, further comprising
a judgment unit configured to judge whether the plurality of fundus images include an invalid area,
wherein the display control unit is configured to control displaying such that in a case where it is determined that there is an invalid area at least in one of the plurality of fundus images, a display form indicating the invalid area is displayed in an area in which the subtraction image is displayed.

14. The image processing apparatus according to claim 13, wherein the display control unit is configured to control displaying such that the display form indicating the invalid area is displayed so as to be superimposed on the invalid area in the subtraction image on the display unit.

15. An image processing apparatus comprising:
a generation unit configured to generate a subtraction image between a plurality of fundus images of an eye corresponding to a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light; and
a display control unit configured to control a display unit to display a marker indicating a position of a two-dimensional tomographic image in at least one of the plurality of three-dimensional tomographic images in a state of being superimposed on the subtraction image.

16. The image processing apparatus according to claim 15, wherein the display control unit is configured to control the display unit to display, when the marker is moved on the displayed subtraction image, the two-dimensional tomographic image corresponding to the position of the marker on the displayed subtraction image.

17. The image processing apparatus according to claim 15, wherein the display control unit is configured to control displaying such that the generated subtraction image and a display form representing a difference between two-dimensional tomographic images corresponding to the position of the marker are displayed side by side on the display unit.

18. The image processing apparatus according to claim 1, wherein
the image processing apparatus is connected to the tomographic imaging unit such that the image processing apparatus and the tomographic imaging unit are allowed to communicate with each other, the tomographic imaging apparatus including a splitting unit and a detection unit, the splitting unit configured to split light obtained by combining light returning from the eye illuminated with measurement light and reference light corresponding to the measurement light into a plurality of light beams polarized in different directions, and the detection unit configured to detect the plurality of light beams polarized in the different direction,
and wherein the generation unit generates the two-dimensional tomographic images of the eye based on the plurality of detected light beams.

19. An image processing apparatus comprising:
a generation unit configured to generate a subtraction image between a plurality of fundus images of an eye corresponding to a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light;
a display control unit configured to control a display unit to display the subtraction image and to display a marker indicating a position of at least one two-dimensional tomographic image in a state of being superimposed on the subtraction image; and
a determination unit configured to determine, by a position of the marker being specified on the displayed subtraction image, the at least one two-dimensional tomographic image using information about at least one of the plurality of three-dimensional tomographic images,
wherein the display control unit is configured to control the display unit to display the determined at least one two-dimensional tomographic image.

20. The image processing apparatus according to claim 19, wherein the determination unit determines the at least one two-dimensional tomographic image by specifying the at least one two-dimensional tomographic image corresponding to the position specified from a plurality of two-dimensional tomographic images forming at least one of the plurality of three-dimensional tomographic images.

21. The image processing apparatus according to claim 19, wherein the determination unit determines the at least one two-dimensional tomographic image by generating the at least one two-dimensional tomographic image corresponding to the specified position using at least one of the plurality of three-dimensional tomographic images.

22. The image processing apparatus according to claim 19, wherein
the display control unit is configured to control displaying such that at least one of the plurality of fundus images is displayed on the display unit, and
when one of the first marker on the displayed subtraction image and the second marker on the displayed at least one fundus image is moved, the other one of the first and second markers is moved accordingly.

23. The image processing apparatus according to claim 19, further comprising
a detection unit configured to detect the specified position of the marker on the displayed subtraction image,
wherein the specifying unit is configured to specify the at least one two-dimensional tomographic image corresponding to the detected position.

24. A method of operating an image processing apparatus, comprising:
generating a subtraction image between a plurality of fundus images of an eye corresponding to a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light;
controlling a display unit to display the subtraction image and to display a marker indicating a position of at least one of a plurality of two-dimensional tomographic images in a state of being superimposed on the subtraction image;

specifying, by a position of the marker being specified on the displayed subtraction image, at least one of the plurality of two-dimensional tomographic images at least one of the plurality of three-dimensional tomographic images; and controlling the display unit to display the specified at least one of the plurality of two-dimensional tomographic images.

25. A method of operating an image processing apparatus, comprising:

generating a subtraction image between a plurality of fundus images of an eye corresponding to a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light; and controlling a display unit to display a marker indicating a position of a two-dimensional tomographic image in at least one of the plurality of three-dimensional tomographic images in a state of being superimposed on the subtraction image.

26. A method of operating an image processing apparatus, comprising:

generating a subtraction image between a plurality of fundus images of an eye corresponding to a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light;

controlling a display unit to display the subtraction image and to display a marker indicating a position of at last one two-dimensional tomographic image in a state of being superimposed on the subtraction image; and determining, by a position of the marker being specified in the displayed subtracted image, the at least one two-dimensional tomographic image based on information about at least one of the plurality of three-dimensional tomographic images, controlling the display unit to display the determined at least one two-dimensional tomographic image.

27. A non-transitory computer-readable storage medium storing a computer program that when executed on a computer causes the computer to perform the method of operation of the image processing apparatus according to claim 24.

28. A non-transitory computer-readable storage medium storing a computer program that when executed on a computer causes the computer to perform the method of operation of the image processing apparatus according to claim 25.

29. A non-transitory computer-readable storage medium storing a computer program that when executed on a computer causes the computer to perform the method of operation of the image processing apparatus according to claim 26.

30. An image processing apparatus comprising:

a generation unit configured to generate an image indicating a change of an eye using a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light; and a display control unit configured to control a display unit to display a marker indicating a position of a two-dimensional tomographic image in at least one of the plurality of three-dimensional tomographic images in a state of being superimposed on the image indicating the change of the eye.

31. The image processing apparatus according to claim 30, wherein the display control unit is configured to control the display unit to display, when the marker is moved on the displayed image indicating the change of the eye, the two-dimensional tomographic image corresponding to the position of the marker on the displayed image indicating the change of eye.

32. The image processing apparatus according to claim 30, wherein the display control unit is configured to control displaying such that the image indicating the change of the eye and a display form representing a difference between two-dimensional tomographic images corresponding to the position of the marker are displayed side by side on the display unit.

33. A method of operating an image processing apparatus, comprising:

generating an image indicating a change of an eye using a plurality of three-dimensional tomographic images, the plurality of three-dimensional tomographic images being obtained by capturing images of the eye at different times using a tomographic imaging unit, the tomographic imaging unit being configured to obtain the plurality of three-dimensional tomographic images using combining light obtained by combining returning light from the eye illuminated with measurement light and reference light corresponding to the measurement light; and controlling a display unit to display a marker indicating a position of a two-dimensional tomographic image in at least one of the plurality of three-dimensional tomographic images in a state of being superimposed on the image indicating the change of the eye.

34. A non-transitory computer-readable storage medium storing a computer program that when executed on a computer causes the computer to perform the method of operation of the image processing apparatus according to claim 33.

* * * * *